(12) United States Patent
Tsai (10) Patent No.: US 9,789,153 B2
(45) Date of Patent: Oct. 17, 2017

(54) COMPOSITION FOR PREVENTING CANCER AND TREATING CANCER AND INTENSIFYING THE EFFECTS OF OTHER ANTICANCER DRUGS

(71) Applicant: Hsiu-Hsien Tsai, Changhua (TW)

(72) Inventor: Hsiu-Hsien Tsai, Changhua (TW)

( * ) Notice: Subject to any disclaimer, the term of this patent is extended or adjusted under 35 U.S.C. 154(b) by 319 days.

(21) Appl. No.: 14/321,839

(22) Filed: Jul. 2, 2014

(65) Prior Publication Data

US 2016/0000856 A1    Jan. 7, 2016

(51) Int. Cl.

| | |
|---|---|
| *A61K 36/9066* | (2006.01) |
| *A61K 36/536* | (2006.01) |
| *A61K 36/539* | (2006.01) |
| *A61K 36/07* | (2006.01) |
| *A61K 36/65* | (2006.01) |
| *A61K 36/84* | (2006.01) |
| *A61K 36/288* | (2006.01) |
| *A23L 33/10* | (2016.01) |
| *A23L 33/105* | (2016.01) |
| *A61K 9/19* | (2006.01) |

(52) U.S. Cl.
CPC .......... *A61K 36/9066* (2013.01); *A23L 33/10* (2016.08); *A23L 33/105* (2016.08); *A61K 36/07* (2013.01); *A61K 36/288* (2013.01); *A61K 36/536* (2013.01); *A61K 36/539* (2013.01); *A61K 36/65* (2013.01); *A61K 36/84* (2013.01); *A23V 2002/00* (2013.01); *A61K 9/19* (2013.01)

(58) Field of Classification Search
CPC .................................................. A61K 36/9066
See application file for complete search history.

(56) References Cited

U.S. PATENT DOCUMENTS

| | | | |
|---|---|---|---|
| 5,411,733 A | 5/1995 | Hozumi et al. | |
| 5,437,866 A | 8/1995 | Sun | |
| 5,595,756 A * | 1/1997 | Bally .................. | A61K 9/1272 264/4.1 |
| 5,837,257 A | 11/1998 | Tsai et al. | |
| 6,998,141 B2 | 2/2006 | Lee | |
| 7,385,088 B1 | 6/2008 | Liu et al. | |
| 7,411,003 B1 | 8/2008 | Liu et al. | |
| 7,456,225 B1 | 11/2008 | Liu et al. | |
| 7,468,392 B1 | 12/2008 | Liu et al. | |
| 7,470,440 B2 | 12/2008 | Newmark et al. | |
| 7,501,454 B2 | 3/2009 | Liu et al. | |
| 7,622,142 B2 | 11/2009 | Newmark et al. | |
| 7,700,136 B2 | 4/2010 | Cohen | |
| 8,173,177 B2 | 5/2012 | Dao et al. | |
| 8,574,636 B2 | 11/2013 | Maimon | |
| 2009/0130101 A1* | 5/2009 | Cohen .................. | A61K 36/539 424/133.1 |
| 2010/0324309 A1* | 12/2010 | Hattori ............... | C07D 207/444 549/261 |

FOREIGN PATENT DOCUMENTS

| | | | |
|---|---|---|---|
| CN | 96115908 A | * | 7/1996 |
| CN | 101755974 A | * | 6/2010 |
| CN | 201310020943 A | * | 1/2013 |
| CN | 103100048 A | * | 5/2013 |
| JP | 2003342183 A | * | 12/2003 |
| KR | 20090119115 A | * | 12/2009 |

OTHER PUBLICATIONS

Chabner et al. Perspectives: Chemotherapy and the War on Cancer; Nature Reviews. Cancer 5.1 (Jan. 2005): 65-72.*
Tassone et al.Novel Therapeutic Approaches Based on the Targeting of Microenvironment-Derived Survival Pathways in Human Cancer: Experimental Models and Translational Issues; Current Pharmaceutical Design 13.5 (Feb. 2007): 487-96.*
The Herbal Encyclopedia. Web archive date Feb. 10, 2003. Retrieved from the internet. URL<http://web.archive.org/web/20030210135948/http://www.naturalark.com/herbcomb.html>. Retrieved on Mar. 31, 2010, 9 pages.*

\* cited by examiner

*Primary Examiner* — Amy L Clark (57) ABSTRACT

This invention relates to a composition derived from Chinese herbal medicines, medicinal plants and extracts thereof, and to its use for preventing cancer and treating cancer and intensifying the effects of other anticancer drugs. More specifically, the composition of the present invention is derived from various Chinese herbal medicines or medicinal plants which have a long history of human consumption. The composition of the invention is obtained through specific techniques and has revealed good cytotoxicities on Malignant Melanoma Cells, Prostate Cancer Cells and Colon Cancer Cells, Lung Cancer Cells, Stomach Cancer Cells, Breast Cancer Cells and Liver Cancer Cells. The composition of the invention has also revealed obvious intensifying the effects of other anticancer drugs. Cancer presents special problems to the medical community which the present invention address.

5 Claims, 8 Drawing Sheets

COMPOSITION FOR PREVENTING CANCER AND TREATING CANCER AND INTENSIFYING THE EFFECTS OF OTHER ANTICANCER DRUGS

TECHNICAL FIELD

This invention relates to a composition derived from Chinese herbal medicines, medicinal plants and extracts thereof, and to its use for preventing cancer and treating cancer and intensifying the effects of other anticancer drugs. More specifically, the composition of the present invention is derived from various Chinese herbal medicines or medicinal plants which have a long history of human consumption. The composition of the invention is obtained through specific techniques and has revealed good cytotoxicities on Malignant Melanoma Cells, Prostate Cancer Cells and Colon Cancer Cells, Lung Cancer Cells, Stomach Cancer Cells, Breast Cancer Cells and Liver Cancer Cells. The composition of the invention has also revealed obvious intensifying the effects of other anticancer drugs. Cancer presents special problems to the medical community which the present invention addresses The present invention relates to a composition, and more particularly relates to a composition for preventing cancer and treating cancer and intensifying the effects of other anticancer drugs. The composition of the present invention comprises PRUNELLAE SPICA ranges from 0.5 to 1.5 weight parts, SCUTELLARIAE BARBATAE HERBA ranges from 0.5 to 1.5 weight parts, *ANTRODIA CAMPHORATA* ranges from 0.5 to 1.5 weight parts, CURCUMAE RHIZOMA ranges from 0.5 to 1.5 weight parts, PAEONIAE SUFFRUTICOSAE CORTEX ranges from 0.5 to 1.5 weight parts, PATRINIAE HERBA ranges from 0.5 to 1.5 weight parts, *IXERIS* HERBA ranges from 0.5 to 1.5 weight parts and *PHELLINUS LINTEUS* ranges from 0.5 to 1.5 weight parts.

Cancer located in the top ten causes of death, which is characterized by an abnormal mass of malignant tissue, resulting from excessive cell division. Cancer cells do not have the limitations of normal cell growth, it can abnormally invade the normal space of other cells. Generally so called 'Cancer' includes Brain Cancer, Head and Neck Cancer, Eye Cancer, Nasopharyngeal Cancer, Oral Cancer, Esophageal Cancer, Lung Cancer, Bronchial Cancer, Mesothelioma, Thyroid Cancer, Breast Cancer, Stomach Cancer, Liver Cancer, Pancreas Cancer, Gall Bladder Cancer, Bile Duct Cancer, Kidney Cancer, Adrenal Cortex Cancer, Pheochromocytoma, Ovary Cancer, Endometrium Cancer, Cervix Cancer, Colorectal Cancer, Cystic Bladder Cancer, Prostate Cancer, Penis Cancer, Testes Cancer, Virginal Cancer, Leukemia, Muscle Cancer, Bone Cancer, Joint Cancer, Lymphoma, Skin Cancer, Nerve cancer, Metastatic Cancer and Sarcoma.

Types of cancer treatment include chemotherapy, surgery, radiation therapy, hormone therapy, biologic therapy, targeted therapy, and combination therapy of these treatments. Chemotherapy is generally carried out by using one or more compounds to inhibit the growth of cancer cells.

Many cancer chemotherapeutic agents have been developed. But due to their side effects, limited efficacy and resistance or other reasons, the medical community is constantly in search of methods and products that will effectively treat cancer. In addition, more people prefer more moderate Traditional Chinese Medicine for cancer treatment.

Traditional Chinese Medicine is generally regarded as more moderate, and has a high market acceptance. So if a pharmaceutical composition can really be proved to have killing cancer cells activity, it will be a considerable benefit for the treatment of cancer. The main purpose of the present invention is to provide a composition for killing cancer cells.

BACKGROUND OF THE INVENTION

Modem medical science is constantly searching for new and more powerful agents to prevent and treat cancer. Cancer of humans and domestic animals cost several billions to several ten billions of dollars annually. Vast sums of money are spent each year by pharmaceutical companies to identify, characterize, and produce new anticancer drugs to combat the emerging drug resistant strains which have become a serious problem. Reliable prophylactic treatments for disease prevention are also of major interest.

Many cancer chemotherapeutic drugs have been developed. But due to their side effects, limited efficacy and resistance or other reasons, the medical community is constantly in search of methods and products that will effectively treat cancer. In addition, more people prefer more moderate Traditional Chinese Medicine for cancer treatment.

Traditional Chinese Medicine is generally regarded as more moderate, and has a high market acceptance. If a pharmaceutical composition can really be proved to have killing cancer cells activity. It will be a considerable benefit for the treatment of cancer.

The composition of this invention is administered to the subject by orally or nasally or cutaneously or parentally or anally or virginally or by spray inhalation or by implanted reservoir or operation or acupuncture. When the composition of this invention is administered to a subject by orally, it is in a form selected from the group consisting of pills, tablets, jellies, lozenges, powders, candies, confections, gels, nutritional supplements, chewing gums, medical nutritionals, beverages, yogurts, milk and aqueous solutions, nutritional product or pharmaceutical product.

The utilities of herbal drugs and folk medicines have been known for thousands of years in China. These herbal approaches to the treatment of numerous illnesses, from arthritis to viral infections, have been viewed by western modern medicine as ineffective and dangerous. Records of the use of herbs date from ancient China, Egypt and Biblical times. Early physicians used hundreds of herbs to treat a variety of ailments. The practice is still widespread, especially in Asia and Europe. During the 19th century, many home remedies containing herbs were patented and sold. Modern drugs have replaced those remedies, but many modern drugs contain ingredients derived from herbs.

In 1776, the English botanist and physician William Withering learned that an herbal tea made by an old farm woman was effective in treating dropsy, or excess water in the tissues, which is caused by the inability of the heart to pump strongly enough. He found that one ingredient of the tea, which was made with leaves of the foxglove plant, strengthened the heart's pumping ability. The drug made from the foxglove plant is now known as digitalis. Besides, Monroe E. Wall and Mansukh C. Wani in the U.S. National Cancer Institute isolated chemotherapeutic drug paclitaxel (taxol) from the Pacific yew (*Taxus brevifolia*) bark in 1967.

Folk medicine is a relatively modern term to the West and has come to mean the care and treatment of the sick through a variety of herbal medicines. In recent years, folk medicines have become of increasing interest to many people in the western scientific medical community.

PRIOR ART

A Chinese herbal medicine known as PRUNELLAE SPICA is prepared from the dried spica or whole plant of *Prunella vulgaris* or *Prunella vulgaris* subsp. *asiatica* (a.k.a., *Prunella vulgaris* var. *lilachina*). Both plants belong to the family Labiatae. The whole plant can be used as a diuretic and also has antibacterial effects in vitro. The herbal medicine tastes bitter and is nontoxic. Treatment dosage is typically 4 to 110 g per day for the average human. Clinically PRUNELLAE SPICA can be applied to treat hypertension, acute conjunctivitis, acute icteric hepatitis, cervical lymph node inflammation, lymphatic TB, simple goiter, tonsillitis & pharyngitis. Uterus bleeding, epiphora, photophobia, abdominal pain, sore, ulcer and in combination with other herbs to treat eye pain.

T. Hozumi et al. disclose that the spike of *Prunella vulgaris* as an antiherpes viral agent for treating herpes virus infection. See T. Hozumi et al. U.S. Pat. No. 5,411,733 issued on May 2, 1995.

H. H. Tsai et al. disclosed that PRUNELLAE SPICA exhibited anti-HIV activities with 100% suppression on both day 3 and day 4 at 2.5 mg/ml. See H. H. Tsai et al. U.S. Pat. No. 5,837,257 issued on Nov. 17, 1998.

C. Y. Lee disclosed a composition comprising *Codonopsis pilosula, Astragalus membranaceus, Coix Lacyma-Jobi, Eupatorium japonicum, Citrus reticulate, Rostellularia procumbens, Prunella vulgaris, Mesona chinensis, Gardenia jasminoides, Forsythia suspense, Paeonia Veitchii, Rheum officinale, Eupolyphaga sinensis, Hedyotis diffusa, Polygonum perfoliatum, Sophora tonkinensis, Hibiscus syriacus, Arisaema heterophyllum, Lobelia chinensis, Ampelopsis japonica, Rhaponticum uniflorum, Pyrrosia sheareri, Boswellig carterii, Commiphora myrrha, Paris polyphylla, Patrinia villosa, Angelica dehurica, Belamcanda chinensis, Taraxacum mongolicum, Lemmaphyllum microphyllum presl, Gleditsia sinensis, Angelica biserrate* and *Ephedra sinica* was applied to treat lymph node cancer. See C. Y. Lee, Taiwan (R.O.C.) Pat. No. I260226 issued on Aug. 21, 2006.

Y. Maimon disclosed that a composition comprising *Astragalus Membranaceus, Poriae Cocos, Atractylodes Macrocephala, Lycium Chinense, Ligustrum Lucidum, Paeonia Lactiflora, Paeonia Obovata, Glehnia Littoralis, Citrus Reticulata, Ophiopogon Japonicus, Millettia Reticulata, Oldenlandia Diffusa, Scutellaria Barbata* and *Prunella Vulgaris* was applied to minimize the side effects associated with chemotherapy. See Y. Maimon, U.S. Pat. No. 8,574,636 issued on Nov. 5, 2013.

A Chinese herbal medicine known as SCUTELLARIAE BARBATAE HERBA is prepared from the dried whole plant of *Scutellaria barbata, Scutellaria rivularis*, or *Scutellaria dependens* which belong to the family Labiatae. The herbal medicine tastes bitter and should not be consumed by those who have anemia. Pregnant women should avoid taking this herb. Treatment dosage is typically 4 to 300 g per day for the average human. Clinically it can be applied to treat bruises, convulsions, pneumonia, sore throat, abdominal pain and enteritis.

H. H. Tsai et al. disclosed that SCUTELLARIAE BARBATAE HERBA exhibited anti-HIV activities with 92% suppression on day 3 and 94% suppression on day 4 at 2.5 mg/ml. See H. H. Tsai et al. U.S. Pat. No. 5,837,257 issued on Nov. 17, 1998.

I. Cohen disclosed that *Scutellaria barbata* extract (no combination with other herbs) was applied to treat advanced breast cancer and metastatic breast cancer. See I. Cohen. U.S. Pat. No. 7,700,136 issued on Apr. 20, 2010.

A. S. Sun disclosed that a combination comprising extracts of *Letinus edodes* plants, mung bean, *Hedyotis diffusa* (wild) and the herb *Scutellaria barbata* permitted amelioration of malignancies in humans. See A. S. Sun, U.S. Pat. No. 5,437,866 issued on Aug. 1, 1995.

J. Dao et al. disclosed that a composition comprising an ethyl acetate extract of *Ganoderma lucidum*, an ethyl acetate extract of *Salvia miltiorrhiza* and an ethyl acetate extract of *Scutellaria barbata* was applied to be an adjuvant agent for treating colon, lung, breast or prostate cancer. See J. Dao et al., U.S. Pat. No. 8,173,177 issued on May 8, 2012, Y. Maimon disclosed that a composition comprising *Astragalus Membranaceus, Poriae Cocos, Atractylodes Macrocephala, Lycium Chinense, Ligustrum Lucidum, Paeonia Lactiflora, Paeonia Obovata, Glehnia Littoralis, Citrus Reticulata, Ophiopogon Japonicus, Millettia Reticulata, Oldenlandia Diffusa, Scutellaria Barbata* and *Prunella Vulgaris* was applied to minimize the side effects associated with chemotherapy. See Y. Maimon, U.S. Pat. No. 8,574,636 issued on Nov. 5, 2013.

A Chinese herbal medicine known as *ANTRODIA CAMPHORATA* is prepared from the fruiting bodies, mycelia or mixture of both from *Antrodia camphorata*. *Antrodia camphorata* is a perennial mushroom belonging to the order Aphyllophorales, the family Polyporaceae. It is an endemic species in Taiwan. Various compounds extracted from *Antrodia camphorata* have hepatoprotective, Anti-oxidative, anti-inflammatory and anti-cancerous etc. various different effects.

G. Hsiao et al. reported that *A. camphorata* extract was effective in prevention of CCl4-induced hepatotoxicity. See G. Hsiao et al., Anti-oxidative and hepatoprotective effects of *Antrodia* camphorate extract. J. Agric. Food Chem., 2003, 51: 3302~3308.

W. C. Lin et al. reported that fermented mycelia from *Antrodia camphorata* could retard the progression of liver fibrosis induced by CCl4 in rats. See W. C. Lin et al. Filtrate of fermented mycelia from *Antrodia camphorata* reduces liver fibrosis induced by carbon tetrachloride in rats World J Gastroenterology 2006 April; 12(15): 2369~2374.

S. Y. Liu et al. disclosed cyclohexenone compounds of *Antrodia camphorata* which inhibited synthesis of HbsAg and HbeAg effectively to achieve the goal of HBV inhibition. See S. Y. Liu et al., U.S. Pat. No. 7,411,003 issued on Aug. 12, 2008.

S. Y. Liu et al disclosed cyclohexenone compounds of *Antrodia camphorata* which decreased the liver damage and the oxidative pressure caused by free radicals, enhanced the antioxidant ability and achieved the purposed of liver protection. See S. Y. Liu et al., U.S. Pat. No. 7,456,225 issued on Nov. 25, 2008.

C. H. HUANG et al., reported that Niuchangchih (*Antrodia camphorata*), especially at a high dosage (0.1 g/kg BW/day), not only showed a hypercholesterolemic effect but also reduced hepatic lipids in alcohol-fed rats. See C. H. Huang et al. Fruiting body of Niuchangchih (*Antrodia camphorata*) protects livers against chronic alcohol consumption damage. J Agric Food Chem. 2010 Mar. 24; 58(6):3859~3866.

T. Y. SONG et al. reported the dry matter of fermented filtrate (DMF) had the strongest antioxidant activity in different solvent extracts of *A. camphorata* in submerged culture (ACSC). See T. Y. SONG et al. Protective Effects of Fermented Filtrate from *Antrodia camphorata* in Submerged Culture against CCl4-Induced Hepatic Toxicity in Rats. J. Agric. Food Chem. 2003, 51, 1571~1577.

Chuian-Fu KEN et al. reported that the recombinant Ac-catalase (catalase from *Antrodia camphorata*) could enzymatically detoxify.OH. See Chuian-Fu KEN et al., Biochemical characterization of a catalase from *Antrodia camphorata*: Expression in *Escherichia coli* and enzyme properties, Botanical Studies (2008) 49: 119~125.

Y. k. Rao et al. reported that the anti-inflammatory effect of CHCl3 and MeOH extracts of *Antrodia camphorata*, was due to the inhibition of macrophage-mediated inflammatory mediators. See Y. k. Rao et al. Evaluation of the anti-inflammatory and anti-proliferation tumor cells activities of *Antrodia camphorata, Cordyceps sinensis,* and *Cinnamomum osmophloeum* bark extracts. Journal of Ethnopharmacology, 2007 October, 114(1):78~85.

S. Y. Liu et al disclosed cyclohexenone compounds of *Antrodia camphorata* which could promote the metabolism of creatine phosphate kinase and blood ammonia in human bodies, were beneficial to their recovery, and then achieved the function in delaying physiological fatigue. See S. Y. Liu et al. U.S. Pat. No. 7,468,392 issued on Dec. 23, 2008.

S. Y. Liu et al. disclosed cyclohexenone compounds of *Antrodia camphorata* used to treat autoimmune diseases. See S. Y. Liu et al. U.S. Pat. No. 7,501,454 issued on Mar. 10, 2009.

J. J. Liu et al. reported that a unique polysaccharide component from *A. camphorata* mycelia had pronounced anti-tumor effects on both in vitro and in vivo model. See J. J. Liu et al. Antitumor effects of the partially purified polysaccharides from *Antrodia camphorata* and the mechanism of its action. Toxicol. Appl. Pharmacol, 2004, 201: 186~193.

C. Y. Lee disclosed a medication combination comprising Baizhu, Danggui, Hanxincao, Huotanmucao, Ainaxiang, Shuodiao, Malan, Ludou, Ganger, Daqinggen, Banbianlian, Xingren, Nuzhenzi (*Antrodia camphorata*), Qianhu, Jiatonghao, Yinchenhao, Yujin, Zhishi, and Banxia for hepatoma and pancreatic cancer. See C. Y. Lee. U.S. Pat. No. 6,998,141 issued on Feb. 14, 2006.

Y. C. Lu et al. reported the effect of *Antrodia camphorata* dimethyl sulfoxide extract on MG63 human osteosarcoma cells, while (25~50 μg/ml) AC did not affect cell viability, but at 100~200 μg/ml AC decreased viability and induced apoptosis in a concentration-dependent manner. See Y. C. Lu et al. Effects of *Antrodia camphorata* on viability, apoptosis, [Ca2+], and MAPKs phosphorylation in MG63 human osteosarcoma cells. Drug Dev. Res, 2007, 68: 71~78.

C. Y. Chang et al. reported that *Antrodia camphorata* ethanol extract, when combined with antitumor agents, showed adjuvant antiproliferative effects on hepatoma cells (in vitro) and on xenografted cells in tumor-implanted nude mice (in vivo). See C. Y. Chang et al. The adjuvant effects of *Antrodia* camphorate extracts combined with anti-tumor agents on multidrug resistant human hepatoma cells. J. Ethnopharmacol, 2008, 118: 387~395.

S. Y. Liu et al. disclosed a novel compound and use thereof, in particular to Antroquinonol B and Antroquinonol C isolated from *Antrodia camphorata* extracts which could effectively inhibit the growth of cancer cells. See S. Y. Liu et al. U.S. Pat. No. 7,385,088 issued on Jun. 10, 2008.

S. L. Li et al. reported that ethanol extracts of *Antrodia camphorata* co-fermented with *Radix Glycyrrhizae* and soybean augmented anti-tumor effects of *Antrodia camphorata* in human hepatoma cells, See S, L. Li et al. The Augmented Anti-Tumor Effects of *Antrodia camphorata* Co-Fermented with Chinese Medicinal Herb in Human Hepatoma Cells, The American Journal of Chinese Medicine, 2009, 37, 4, 771~783.

C. C. Huang et al. reported the effect of *Antrodia camphorata* dimethyl sulfoxide extract on OC2 Human Oral Cancer Cells, while 25 μg/ml AC significantly increased viability, 100~200 μg/ml AC decreased viability in a concentration-dependent manner. See C. C. Huang et al. Effects of *Antrodia camphorata* Extracts on the Viability, Apoptosis, [Ca2+]i, and MAPKs Phosphorylation of OC2 Human Oral Cancer Cells, Chinese Journal of Physiology, 2009; 52(3): 128~135.

G. M. Lai et al. disclosed a mevalonate pathway inhibitor enhanced the efficacy of an *Antrodia camphorata* extract in treating cancer. As a result, a lower dose of the *Antrodia camphorata* extract was required to obtain desired therapeutic efficacy. See G. M. Lai et al., Taiwan (R.O.C.) Pat. No. I311912 issued on Jul. 11, 2009.

T. I. Chen et al. reported that in a 90-day subchronic toxicological assessment no-observed-adverse-effect level of *Antrodia* is identified to be greater than 3000 mg/kg BW/day in Sprague-Dawlly rats. See T. I. Chen et al., A 90-day subchronic toxicological assessment of *Antrodia cinnamomea* in Sprague-Dawley rats. Food and Chemical Toxicology 2011 February; 49(2):429~433

A Chinese herbal medicine known as CURCUMAE RHIZOMA is prepared from the dried rhizome of *Curcuma longa, Curcuma aromatica, Curcuma aeruginosa, Curcuma zedoaria, Curcuma xanthorrhiza* or *Curcuma phaeocaulis*. These plants belong to the family Zingiberaceae. Their functions are activation and decongestion of blood flow and pain relief. Treatment dosage is typically 3 to 12 g per day for the average human. CURCUMAE RHIZOMA can also be combined with other herbs or drugs to protect liver or treat cancer.

N. KAORU et al. disclosed a turmeric-containing composition characterized by containing turmeric together with squalene or squalane as the active ingredients, which is capable of fully exhibiting usefulness in protecting and improving liver functions. See N. KAORU et al. Taiwan (R.O.C.) Pat. No. I277422 issued on Apr. 1, 2007.

C. Y. Lee disclosed a medication combination comprising Baizhu, Danggui, Hanxincao, Huotanmucao, Ainaxiang, Shuodiao, Malan, Ludou, Ganger, Daqinggen, Banbianlian, Xingren, Nuzhenzi, Qianhu, Jiatonghao, Yinchenhao, Yujin (*Curcuma aromatica*), Zhishi, and Banxia for hepatoma and pancreatic cancer. See C. Y. Lee. U.S. Pat. No. 6,998,141 issued on Feb. 14, 2006.

T. Newmark et al. disclosed a composition comprising hydroalcoholic extracts of holy basil, ginger, turmeric (*Curcuma longa*), *Scutellaria baicalensis*, rosemary, green tea, huzhang, Chinese goldthread, and barberry for treating prostate cancer. See T. Newmark et al. U.S. Pat. No. 7,470,440 issued on Dec. 30, 2008.

T. Newmark et al. disclosed a composition comprising hydroalcoholic extracts of holy basil, ginger, turmeric (*Curcuma longa*), *Scutellaria baicalensis*, rosemary, green tea, huzhang, Chinese goldthread, and barberry for treating glioblastoma. See T. Newmark et al. U.S. Pat. No. 7,622,142 issued on Nov. 24, 2009.

C. Y. Lee et al. disclosed that a composition comprising Cow bile, *Curcuma aromatica* (bark), *Rhinoceros unicornis* L., Scutellaria baicalnsis, Coptis teetoides, realgar, Fructus gareniae jasminoidis, Cinnabaris, Borneol, Moschu secretio, Margarita, gold the mixture thereof was applied to prevent reperfusion lesions after cerebral ischemia. See C. Y. Lee et al, Taiwan (R.O.C.) Pat. No. I353846 issued on Dec. 11, 2011

Curcumin, the main ingredient of CURCUMAE RHIZOMA, was used as health food for cancer prevention and anti-oxidation.

A Chinese herbal medicine known as PAEONIAE SUFFRUTICOSAE CORTEX is prepared from the dried root skin of *Paeonia suffruticosa, Paeonia suffruticosa* var. *spontanea, Paeonia papaveracea, Paeonia szechuanica, Paeonia lutea, Paeonia delavayi, Paeonia potanini, Paeonia thalictrumifolia* or *Paeonia yunnanonsis* which belong to the family Ranunculaceae. PAEONIAE SUFFRUTICOSAE CORTEX should not be consumed by those who have Hypermenorrheah, Pregnancy, Diarrhea or Perspiration. Clinically it can be applied to treat purpura, convulsions, hematemesis, epistaxis, bloody stool passage and amenorrhea. Treatment dosage is typically 7 to 12 g per day for the average human.

H. M. Hsieh et al. disclosed a composition comprising *Coptis chinensis, Climicifuga foetida, Angelica sinensis Rehmannia glutinosa* and *Paeonia suffruticosae* cortex for inhibiting lung cancer stem cell. See H. M. Hsieh et al. Taiwan (R.O.C.) Pat. No. I413525 issued on Dec. 1, 2013.

A Chinese herbal medicine known as PATRINIAE HERBA is prepared from the dried whole plant of *Patrinia scabiosaefolia* or *Patrinia villosa*. Treatment dosage is typically 10 to 20 g per day for the average human. Clinically PATRINIAE HERBA can be applied to treat infectious diseases: influenza, mumps, acute conjunctivitis, tonsillitis, acute pancreatitis, pneumonia, liver abscess, gastroenteritis, hematemesis, epistaxis and neurosis.

C. Y. Lee disclosed a composition comprising *Codonopsis pilosula, Astragalus membranaceus, Coix Lacyma-Jobi, Eupatorium japonicum, Citrus reticulate, Rostellularia procumbens, Prunella vulgaris, Mesona chinensis, Gardenia jasminoides, Forsythia suspense, Paeonia Veitchii, Rheum officinale, Eupolyphaga sinensis, Hedyotis diffusa, Polygonum perfoliatum, Sophora tonkinensis, Hibiscus syriacus, Arisaema heterophyllum, Lobelia chinensis, Ampelopsis japonica, Rhaponticum uniflorum, Pyrrosia sheareri, Boswellig carterii, Commiphora myrrha, Paris polyphylla, Patrinia villosa, Angelica dehurica, Belamcanda chinensis, Taraxacum mongolicum, Lemmaphyllum microphyllum presl, Gleditsia sinensis, Angelica biserrate* and *Ephedra sinica* was applied to treat lymph node cancer. See C. Y. Lee, Taiwan (R.O.C.) Pat. No. I260226 issued on Aug. 21, 2006.

A Chinese herbal medicine known as *IXERIS* HERBA is prepared from the dried whole plant of *Ixeris chinensis*. Treatment dosage is typically 10 to 40 g per day for the average human. Clinically *IXERIS* HERBA can be applied to treat pneumonia, sore throat, diphtheria, enteritis, cystitis, hemorrhoid and urolithiasis. Besides, *IXERIS* HERBA can be combined with other herbs to be a health product for helping woman growing. See Z. I. Tsai, Taiwan (R.O.C.) Pat. No. M376295 issued on Mar. 21.2010.

A Chinese herbal medicine known as *PHELLINUS LINTEUS* is prepared from the fruiting bodies, mycelia or mixture of both from *Phellinus linteus*. *Phellinus linteus* is a perennial mushroom belonging to the order Hymenochaetales, the family Hymenochaetaceae. *Phellinus linteus* have been widely used in Japan, Korea and China. *Phellinus linteus* is effective on various diseases such as improving blood circulation, enhancing detoxication, hepatoprotection of human body, combating allergy and diabetes, curing oral ulcer and alleviating gastroenteric disorder or lymphatic disease. Extracts from *Phellinus linteus* were reported to posse immunoregulatory and anti-cancer effects. *Phellinus linteus* is an excellent herbal source of anti-oxidants and liver protecting agents. See T. Zhu et al. A Medicinal Mushroom: *Phellinus linteus*. Current Medicinal Chemistry 2008, 15: 1330~1335

SUMMARY OF THE INVENTION

As used herein and in the claims, the following nomenclatures will be used to identify the single-herb components of the composition. The present invention in its broadest aspect relates to the use of the described herbal composition thereof to prevent and treat various cancers. More specifically, the composition of the invention has also revealed obvious intensifying the effects of other anticancer drugs. The herbs used as starting materials for this invention may be obtained from commercial sources as single-herb herbal medicines which may be mixed, or extracted and concentrated, and placed in composition for the administration to a human. The plant extracts, once isolated from the plant material, may be concentrated and then placed in composition for the administration to a human. The composition of this invention may take a variety of forms such as capsules, tablets, powder, candies, gels, beverages, teas, nutritional products, and the like.

The dosage of the composition of the invention can range from 0.4 to 120 g per day for the mammal in need of therapy. More specifically, the dosages for a given composition can range from 0.4 to 100 g per day One skilled in the art will appreciate that depending upon the weight of the individual and the progression of the cancer, that higher doses of the compositions will be required. One skilled in the art can tailor each dosage rate for a given individual without undue experimentation. Preferably, the dosages for a given composition can range from 10 to 25 g per day. Preferably, the compositions are administered at least three (3) times per day however, bolus administration will be effective. It will be appreciated that the dosages recited herein are for the herbal medicine (extract deposited on ground plant) in dry form. Further, extracts of the inventive compositions will increase the concentration of the actives and therefore reductions in the dosage levels will be realized. Dosages as low as 10% of those recited herein for the inventive compositions are contemplated.

The composition of the invention is preferably administered enterally, however, intravenous (i.v.) and/or intramuscular (i.m.) administration is also contemplated herein. Those skilled in the art will understand how i.v. and i.m. formulations can be prepared and how the effective dosages can be obtained.

In a preferred embodiment, the herbal composition is incorporated into oral dosage forms such as capsules, tablets, teas, powders, candies, candy bars, beverages, nutritional products, and the like.

Also disclosed is a medicinal product produced by the process comprising the steps of a) contacting comminuted plant material of PRUNELLAE SPICA, SCUTELLARIAE BARBATAE HERBA, *ANTRODIA CAMPHORATA*, CURCUMAE RHIZOMA, PAEONIAE SUFFRUTICOSAE CORTEX, PATRINIAE HERBA, *IXERIS* HERBA and *PHELLINUS LINTEUS*, with water to form an aqueous plant material; b) heating the aqueous plant material to about 100.degree. C. and holding at that temperature for about 0.5 to about 3 hours; c) separating the insoluble plant material from the aqueous phase; and d) concentrating the solute contained in the aqueous phase. The concentrated solute may then be subjected to freeze drying, spray drying, evaporation or ultrafiltration.

Specific details and descriptions of the above recited Chinese herbal medicines and medicinal herbs can be found in the following references:
(1) W. S. Kan, Pharmaceutical Botany, National Research Institute of Chinese Medicine, Taipei, Taiwan (R.O.C.): 271,485, 532,641, 642,643 (1973); (2) J. P. Lin, Chinese Medicine Pharmacology and Applications I, Chinese Medical College, Taichung, Taiwan (R.O.C.): 201~207, 236~246 (1985);
(3) N. Y. Chiu & K. H. Chang, The Illustrated Medicinal Plants of Taiwan I, SMC Publishing Co., Taipei, Taiwan (R.O.C.): 186, 188 (1995);
(4) N. Y. Chiu & K. H. Chang, The Illustrated Medicinal Plants of Taiwan II, SMC Publishing Co., Taipei, Taiwan (R.O.C.): 245 (1995); (5) N. Y. Chiu & K. H. Chang, The Illustrated Medicinal Plants of Taiwan IV, SMC Publishing Co., Taipei, Taiwan (R.O.C.): 81 (1995); (6) H. C Chang, Medicinal Herbs I, Holiday Publishing Co. Taipei, Taiwan (R.O.C.): 15 (1997); (7) H. C Chang, Medicinal Herbs II, Holiday Publishing Co. Taipei, Taiwan (R.O.C.): 15 (1997); (8) M. S. Lee & W. Z. Lee, Frequently Used Chinese Crude Drugs Handbook, National Research Institute of Chinese Medicine, Taipei, Taiwan (R.O.C.): 30, 44, 62, 85, 98, 103, 133, 142 (2001).

It is noted that in the practice of Chinese traditional medicine, herbal medicines were used to treat the symptoms of the patients, not the disease entity itself, and were therefore fairly nonspecific to a particular disease. Herbal medicines were used depending on the symptoms of the individual patient. The composition of herbal medicines would vary case by case and may even change for each individual patient during the course of the treatment according to each treatment result. It is therefore very difficult to have a universal herbal composition suitable for treating a specific disease within a population.

The present invention is directed to the discovery of anticancer herbal composition, extracts thereof. The anticancer herbal composition of this invention is derived from individual herbs, herb mixtures and commercially available Chinese herbal medicines. This novel herbal composition has demonstrated activities against various cancer cells. The composition of the invention has also revealed obvious intensifying the effects of other anticancer drugs. This application sets forth the data available on the present discoveries and fully describes the composition of matter, its preparation, and clinical applications. These and other aspects of the invention will become apparent to those skilled in the art as a result of the following examples which are intended as illustrative of the invention and not limitative.

BEST MODE FOR CARRYING OUT THE INVENTION

For acquaint persons skilled in the art with the principles of the invention, the following Examples are submitted.

Example 1

Preparation of Herb Composition

In the preparation of the herbal composition according to the invention, Chinese herbal medicines in single herb format were obtained from commercial sources in powder form. The individual single-herb herbal medicines were mixed with the same weight to prepare the herbal composition. The herbal composition was prepared by mixing equal weights of 8 single-herb herbal medicines PRUNELLAE SPICA, SCUTELLARIAE BARBATAE HERBA, *ANTRODIA CAMPHORATA*, CURCUMAE RHIZOMA, PAEONIAE SUFFRUTICOSAE CORTEX, PATRINIAE HERBA *IXERIS* HERBA and *PHELLINUS LINTEUS*. It is noted that a composition of decoctions prepared individually from the source plants of the single-herb herbal medicines or a decoction prepared from the pre-mixed source plants of the single-herb components of the herb mixture is well within the specification of the herb mixture.

Example 2

Preparation of Single-Herb Herbal Medicines

Each single-herb herbal medicine used to prepare the herbal Composition has been described in the Prior Art section of this application. The plant source from which each single-herb herbal medicine is obtained was also listed in the Prior Art section. More than one species or genus of medicinal plant may be used to prepare the same herbal medicine as indicated in the plant source list of that herbal medicine. For example, the herbal medicine PRUNELLAE SPICA may be prepared from *Prunella vulgaris* or *Prunella vulgaris* subsp. *asiatica* (a.k.a., *Prunella vulgaris* var. *lilachina*). The herbal medicine SCUTELLARIAE BARBATAE HERBA may be prepared from *Scutellaria barbata*, *Scutellaria rivularis*, or *Scutellaria dependens*. The herbal medicine PAEONIAE SUFFRUTICOSAE CORTEX may be prepared from *Paeonia suffruticosa*, *Paeonia suffruticosa* var. *spontanea*, *Paeonia papaveracea*, *Paeonia szechuanica*, *Paeonia lutea*, *Paeonia delavayi*, *Paeonia potanini*,

*Paeonia thalictrumifolia* or *Paeonia yunnanonsis* hereof. The herbal medicines were prepared from their respective plant sources as follows.

A suitable part or parts or the whole herb of a medicinal plant was obtained, washed with cold water, dried and comminuted. The plant materials were then extracted with boiling water on a basis of 1 part by weight of plant material to approximately 5 to 10 parts by weight of water. The amount of water used should at least cover the plant material in the extraction vessel. Samples were boiled for 0.5 to one hour, but not in excess of 3 hours, in order to allow effective extraction of the desired components. Shorter or longer heating would not substantially affect the extraction, except the yield and cost. The aqueous solution was separated from the plant material by filtration. The aqueous solution may be freeze dried or spray dried, or reduced in volume by heating with or without an applied vacuum. The concentrate may then be spray dried or freeze dried or absorbed by powdered material of the same plant material or starch and thus the single-herb herbal medicine is prepared in powdered form.

It is noted that a decoction prepared from a source plant of the single-herb herbal medicine is well within the specification. A decoction is the aqueous solution of the plant material prepared by boiling the plant material in water as described above for about 0.5 to one hour. The decoction may be directly consumed after it is prepared and cooled to warm or ambient temperatures or preserved with proper sterilization for later consumption. Sterilization may be accomplished by microfiltration or heat.

Herbal composition extract for cytotoxicity test on cancer cell with MTT assay

MTT (3-(4,5 dimethylthiazole-2-yl)-2,5-diphenyl tetrazolium bromide) is a proven cell viability indicator and this yellow colored tetrazolium salt gets reduced to purple colored formazan crystals by mitochondrial reductase enzyme seen only in metabolically active cells. It measures the cell proliferation rate and the reduction in cell viability when metabolic events lead to apoptosis or necrosis. Triplicate samples were analyzed and cell viability was calculated in percentage with respect to negative control group as follows Cell viability (%)=($Nt/Nc$)×100

Nt is the absorbance of cells treated with sample and Nc is the absorbance of untreated cells (negative control group-Cell culture medium alone). The cell survival rate of negative control group is 100%. The results of MTT assays are shown in Figures, Wherein, the horizontal axis represents concentration of test sample and the vertical axis represents the cell survival rate.

Cell Culture Medium:
C1-A: DMEM with 10% FBS (fetal bovine serum), 100 units/ml Penicillin and 100 ug/ml Streptomycin
C1-B: RPMI1640 with 10% FBS (fetal bovine serum), 100 units/ml Penicillin and 100 ug/ml Streptomycin
C1-C: MEM with 10% FBS (fetal bovine serum), 100 units/ml Penicillin and 100 ug/ml Streptomycin
C1-D: F-12K with 10% FBS (fetal bovine serum), 100 units/ml Penicillin and 100 ug/ml Streptomycin
MTT Assay-A:

Cancer cells were incubated for 2 days. Then different cancer cells were seeded in 96 well plate with a seeding density of 10,000 cells per well and incubated for 24 hours. Then the cells were treated with different concentrations of the herb extract. After treatment, the cells were incubated for 4 h with 100 μl of MTT (0.5 mg/ml) in serum-free media. The formazan crystals formed by viable cells were then dissolved by treatment with 100 μl solubilization buffer (10% (v/v) Triton X-100 and 0.1N HCl in isopropanol) for 1 h. Optical density of the solution was measured at a wavelength of 570 nm using a Beckmann Coulter Elisa plate reader (BioTek Power Wave XS).

Cell culture medium alone was used as a Negative control group.

Triton X100 (1%), killing more than 90% cells, was used as a Positive control group marked as C2.
MTT Assay-B:

MTT assay-B is with the same principle and the similar method as MTT assay-A. But Optical density of the solution was measured at a wavelength of 570 nm using a Spectra Max M5 Microplate Reader (Molecular Devices). Besides, there is no positive control group in this assay. The cell survival rate of negative control group is 100%. Negative control group is not shown in FIG.

Example 3

Herbal Composition Extract for Cytotoxicity Test on Melanoma Cell A375

Culture Medium of A375: C1-A

Melanoma Cell survival rate is characterized through MTT assay-A after treating with 0.5 mg/ml, 1 mg/ml, 5 mg/ml and 10 mg/ml of the herbal composition extract according to Example 1 respectively. Negative control group: C1-A. Positive control group: C2.

Figure 1:
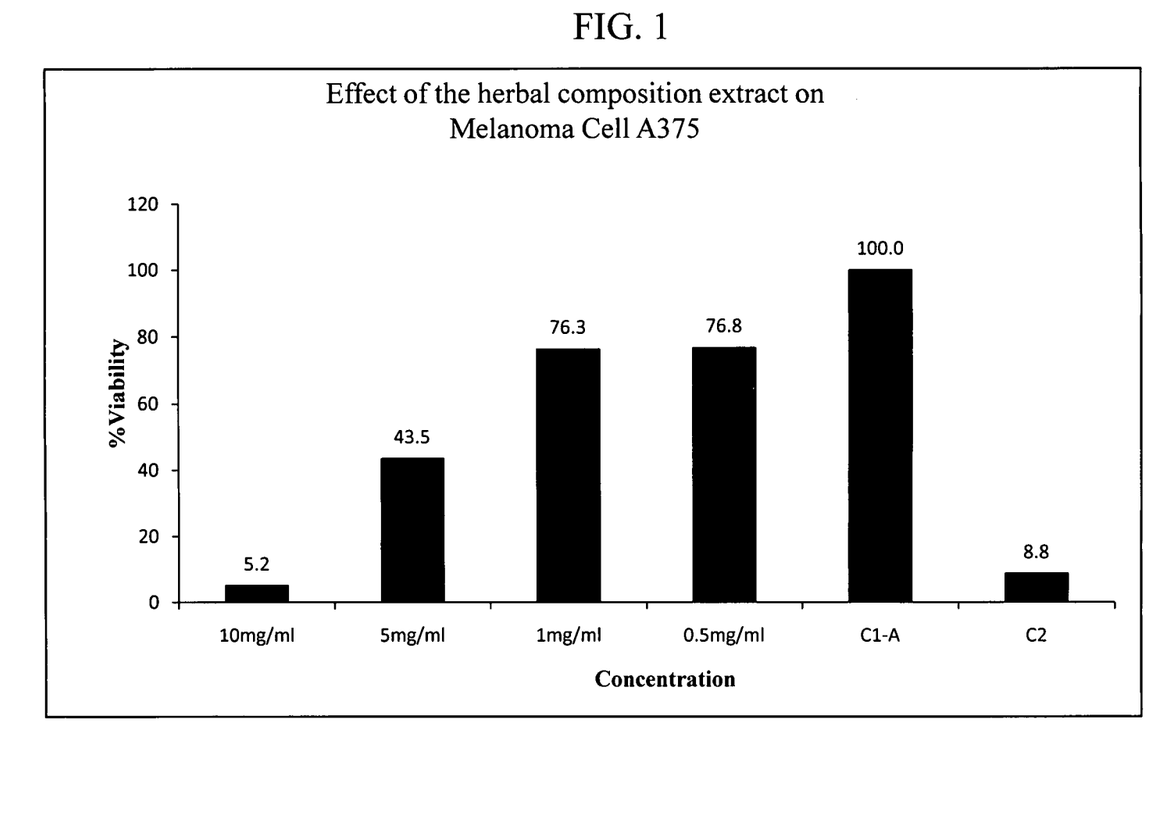
FIG. 1 shows viability of Melanoma Cell A375 treated with 0.5 mg/ml, 1 mg/ml, 5 mg/ml and 10 mg/ml of the herbal composition extract.

FIG. 1 shows that the increased concentration of the herbal composition extract causes the reduction of A375 cancer cell viability after treatment. A concentration-dependent cytotoxic effect of the composition of the invention on Melanoma Cell A375 is found. And pursuant to the experimental results, the calculated 1050 (half inhibition concentration) value is 3.20 mg/ml.

Example 4

Herbal Composition Extract for Cytotoxicity Test on Prostate Cancer Cell PC3

Culture Medium of PC3: C1-A

PC3 Prostate Cancer Cell survival rate is characterized through MTT assay-A after treating with 0.5 mg/ml, 1 mg/ml, 5 mg/ml and 10 mg/ml of the herbal composition extract according to Example 1 respectively. Negative control group: C1-A. Positive control group: C2.

Figure 2:
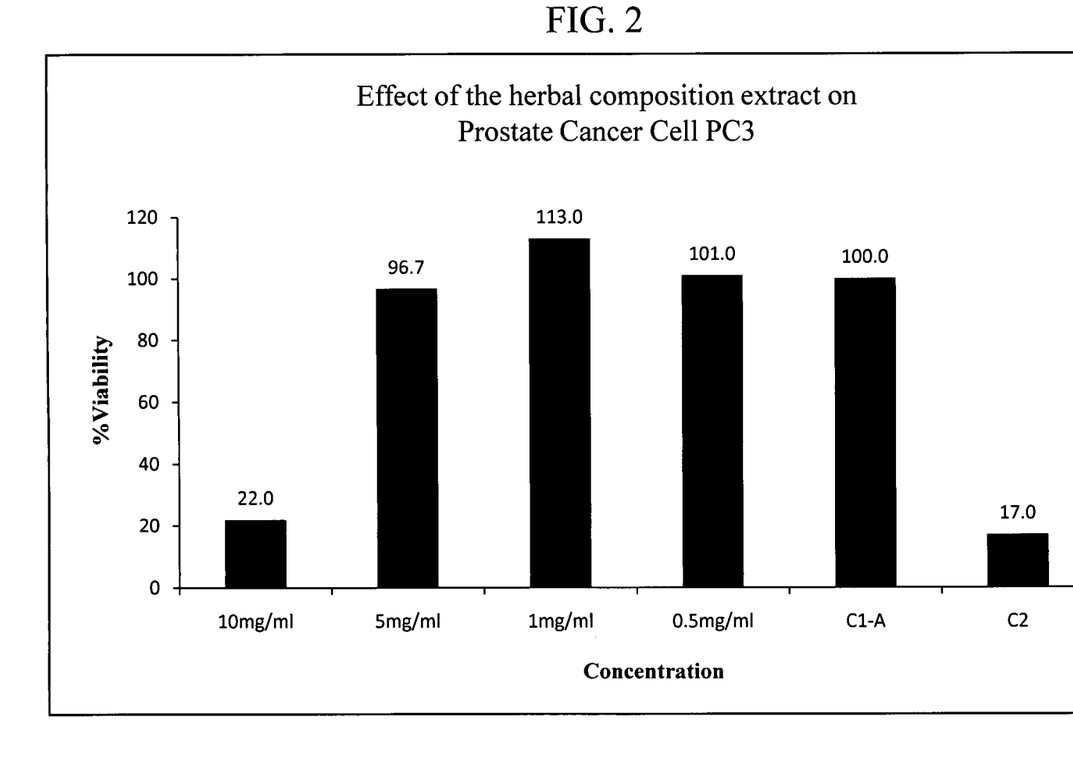
FIG. 2. shows viability of Prostate Cancer Cell PC3 treated with 0.5 mg/ml, 1 mg/ml, 5 mg/ml and 10 mg/ml of the herbal composition extract.

FIG. 2 shows that at 1 mg/ml~10 mg/ml the herbal composition extract causes the reduction of PC 3 cancer cell viability after treatment. A concentration-dependent cytotoxic effect of the composition of the invention on Prostate Cancer Cell PC3 is found. And pursuant to the experimental results, the calculated 1050 value is 8.36 mg/ml.

Example 5

Herbal Composition Extract for Cytotoxicity Test on Colon Cancer Cell HT29

Culture Medium of HT29: C1-B

HT29 Colon Cancer Cell survival rate is characterized through MTT assay-A after treating with 0.5 mg/ml, 1 mg/ml, 5 mg/ml and 10 mg/ml of the herbal composition extract according to Example 1 respectively. Negative control group: C1-B. Positive control group: C2.

Figure 3:
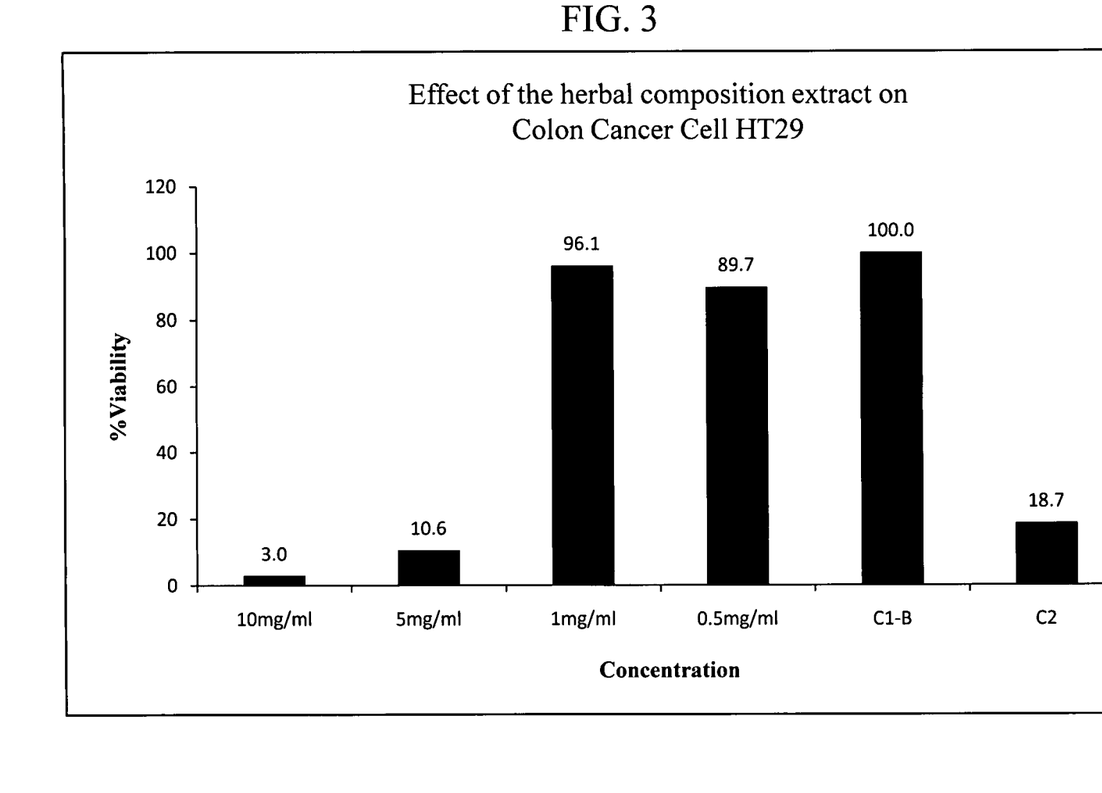
FIG. 3. shows viability of Colon Cancer Cell HT29 treated with 0.5 mg/ml, 1 mg/ml, 5 mg/ml and 10 mg/ml of the herbal composition extract.

FIG. 3 shows that at 1 mg/ml~10 mg/ml the herbal composition extract causes the reduction of HT29 cancer cell viability after treatment.

A concentration-dependent cytotoxic effect of the composition of the invention on Colon Cancer Cell HT29 is found. And pursuant to the experimental results, the calculated IC50 value is 3.47 mg/ml.

Example 6

Herbal Composition Extract for Cytotoxicity Test on Lung Cancer Cell A549

Culture Medium of A549: C1-C

A549 Lung Cancer Cell survival rate is characterized through MTT assay-A after treating with 0.5 mg/ml, 1 mg/ml, 5 mg/ml and 10 mg/ml of the herbal composition extract according to Example 1 respectively. Negative control group: C1-C. Positive control group: C2.

Figure 4:
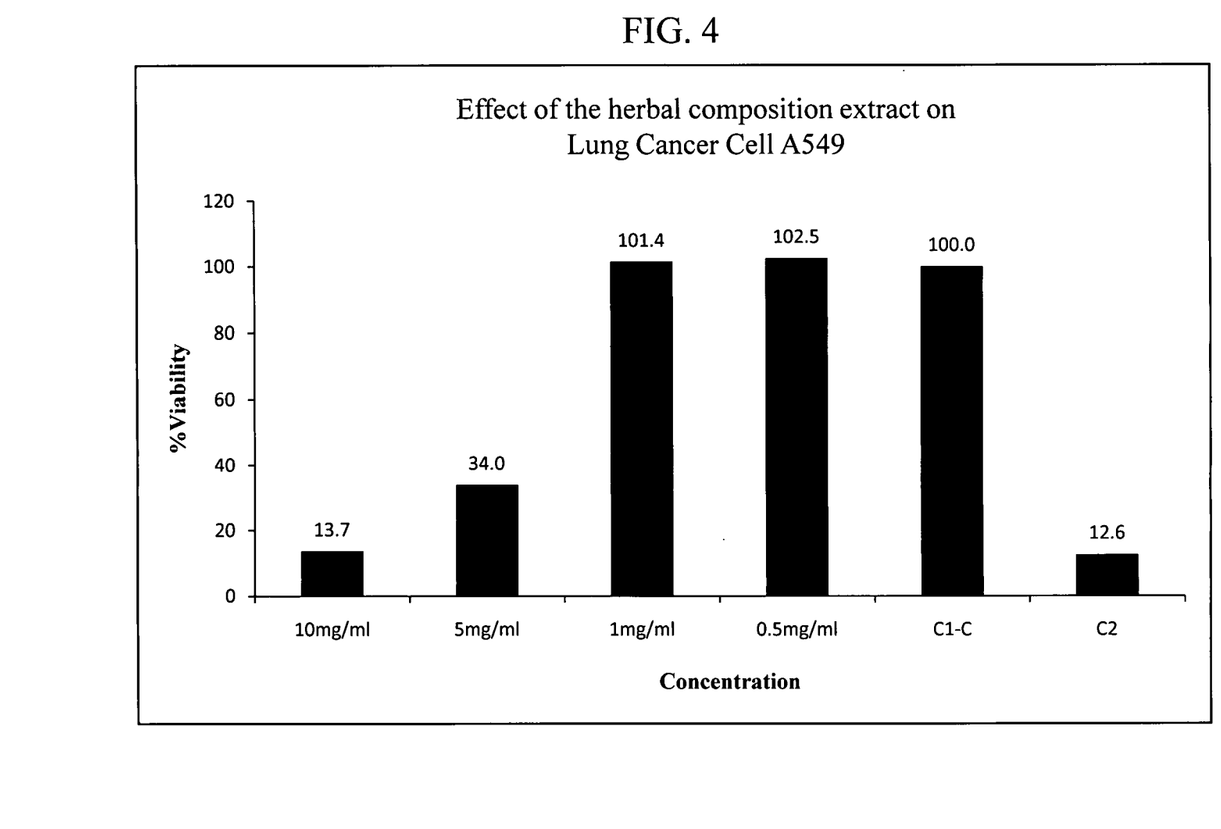
FIG. 4. shows viability of Lung Cancer Cell A549 treated with 0.5 mg/ml, 1 mg/ml, 5 mg/ml and 10 mg/ml of the herbal composition extract.

FIG. 4 shows that the increased concentration of the herbal composition extract causes the reduction of A549 cancer cell viability after treatment. A concentration-dependent cytotoxic effect of the composition of the invention on Lung Cancer Cell A549 is found. The viability of A549 lung cancer cells is only 34% at concentration 5 mg/ml. But pursuant to the experimental results, the calculated IC50 value is 5.04 mg/ml.

Example 7

Herbal Composition Extract for Cytotoxicity Test on Stomach Cancer Cell AGS

Culture Medium of AGS: C1-D

AGS Stomach Cancer Cell survival rate is characterized through MTT assay-B after treating with 0.22 mg/ml, 0.44 mg/ml, 0.87 mg/ml, 1.75 mg/ml, 3.50 mg/ml and 7.00 mg/ml of the herbal composition extract according to Example 1 respectively.

Figure 5:
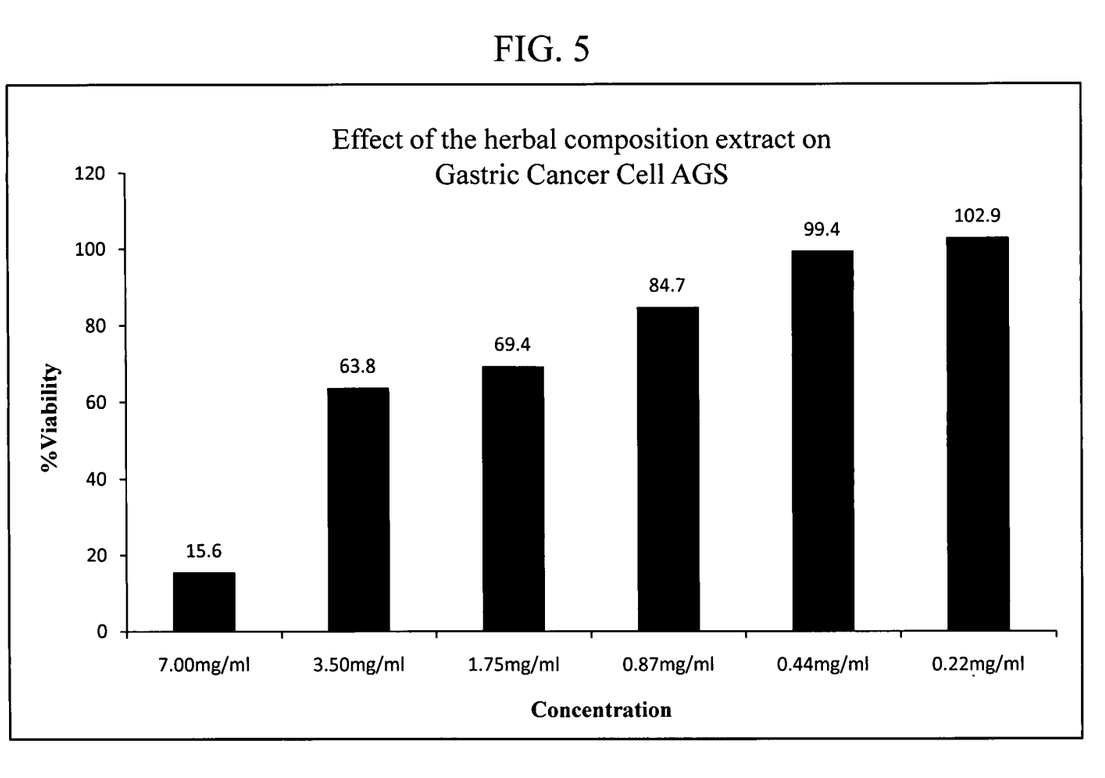
FIG. 5. shows viability of Stomach Cancer Cell AGS treated with 0.22 mg/ml, 0.44 mg/ml, 0.87 mg/ml, 1.75 mg/ml, 3.50 mg/ml and 7.00 mg/ml of the herbal composition extract.

FIG. 5 shows that the increased concentration of the herbal composition extract causes the reduction of A549 cancer cell viability after treatment. A concentration-dependent cytotoxic effect of the composition of the invention on Stomach Cancer Cell AGS is found. And pursuant to the experimental results, the calculated IC50 value is 3.19 mg/ml.

Example 8

Herbal Composition Extract for Cytotoxicity Test on Breast Cancer Cell MCF-7

Culture Medium of MCF-7: C1-C

MCF-7 Breast Cancer Cell survival rate is characterized through MTT assay-B after treating with 0.24 mg/ml, 0.48 mg/ml, 0.95 mg/ml, 1.90 mg/ml, 3.80 mg/ml and 7.60 mg/ml of the herbal composition extract according to Example 1 respectively.

Figure 6:
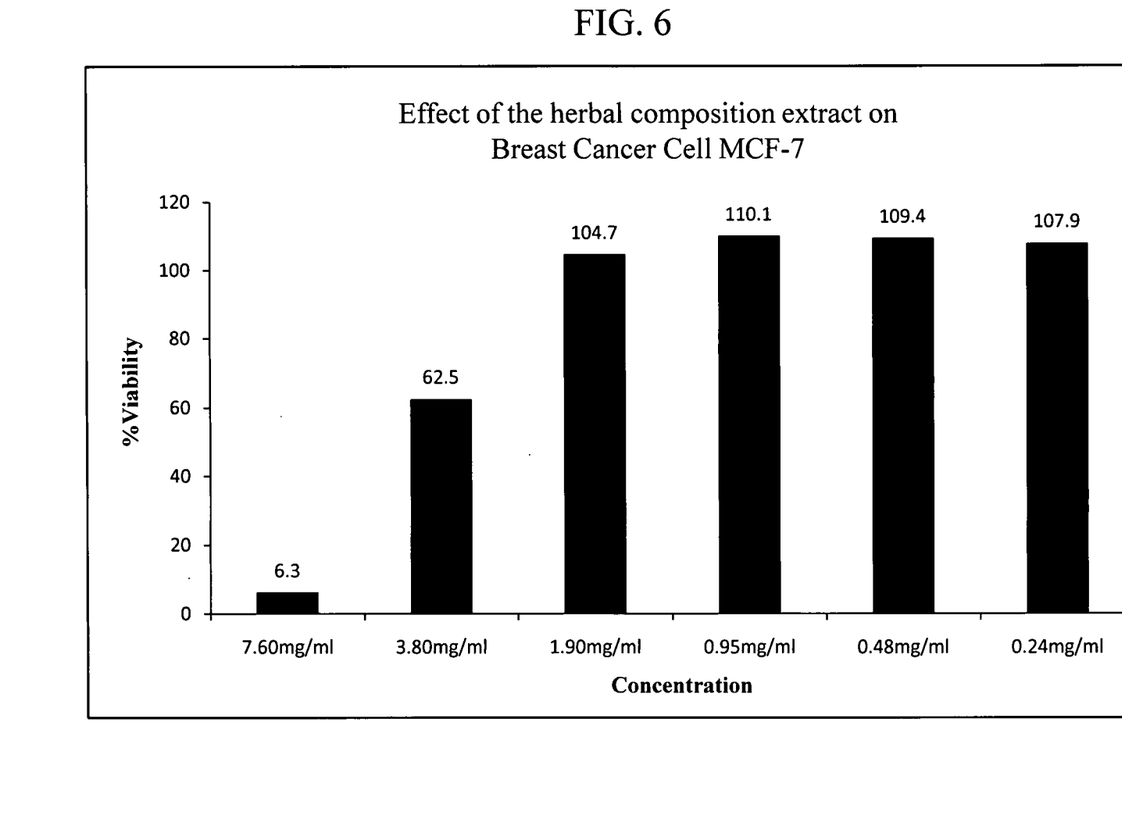
FIG. 6. shows viability of Breast Cancer Cell MCF-7 treated with 0.24 mg/ml, 0.48 mg/ml, 0.95 mg/ml, 1.90 mg/ml, 3.80 mg/ml and 7.60 mg/ml of the herbal composition extract.

FIG. 6 shows that at 0.95 mg/ml-7.60 mg/ml the herbal composition extract causes the reduction of A549 cancer cell viability after treatment. A concentration-dependent cytotoxic effect of the composition of the invention on Breast Cancer Cell MCF-7 is found. And pursuant to the experimental results, the calculated IC50 value is 4.38 mg/ml.

Example 9

Herbal Composition Extract for Cytotoxicity Test on Liver Cancer Cell Huh7

Culture Medium of Huh7: C1-A

Huh7 Liver Cancer Cell survival rate is characterized through MTT assay-B after treating with 0.25 mg/ml, 0.51 mg/ml, 1.01 mg/ml, 2.02 mg/ml, 4.05 mg/ml and 8.09 mg/ml of the herb composition extract according to Example 1 respectively.

Figure 7:
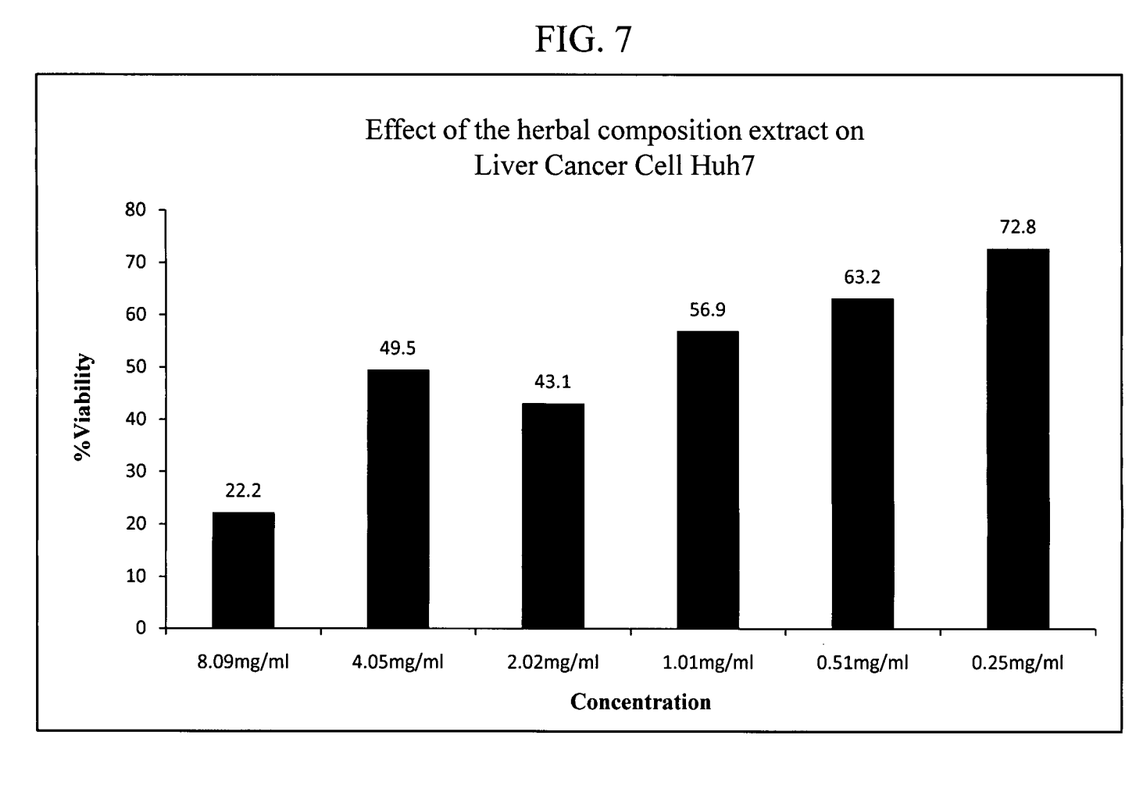
FIG. 7. shows viability of Liver Cancer Cell Huh7 treated with 0.25 mg/ml, 0.51 mg/ml, 1.01 mg/ml, 2.02 mg/ml, 4.05 mg/ml and 8.09 mg/ml of the herbal composition extract.

FIG. 7 shows that the increased concentration of the herbal composition extract causes the reduction of A549 cancer cell viability after treatment. A concentration-dependent cytotoxic effect of the composition of the invention on Liver Cancer Cell Huh7 is found. And pursuant to the experimental results, the calculated IC50 value is 1.50 mg/ml.

Example 10

Herbal Composition Extract in Combination with Different Drugs for Cytotoxicity Test on Colon Cancer Cell HT29

5-FU (5-fluorouracil)—from Celon Lab
Irinotecan—from Dr. Reddy Lab
Oxaliplatin—from Panacea Biotech
Culture Medium of HT29: C1-B HT29 Colon Cancer Cell survival rate is characterized through MTT assay-A after treating with S1: Herb extract 5 mg/ml, S2: 5-FU 5 ug/ml, S3: Oxaliplatin 10 ug/ml, S4: Irinotecan5 ug/ml, S5: Herb extract 5 mg/ml and 5-FU 5 ug/ml, S6: Herb extrac5 mg/ml and Oxaliplatin 10 ug/ml, S7: Herb extract 5 mg/ml and Irinotecan 5 ug/ml, S8: Herb extract 5 mg/ml and 5-FU 5 ug/ml and Oxaliplatin 10 ug/ml, S9: Herb extract 5 mg/ml and 5-FU 5 ug/ml and Irinotecan 5 ug/ml, S10: 5-FU 5 ug/ml and Oxaliplatin 10 ug/ml, S11: 5-FU 5 ug/ml and Irinotecan 5 ug/ml. Negative control group: C1-B. Positive control group: C2.

Figure 8:
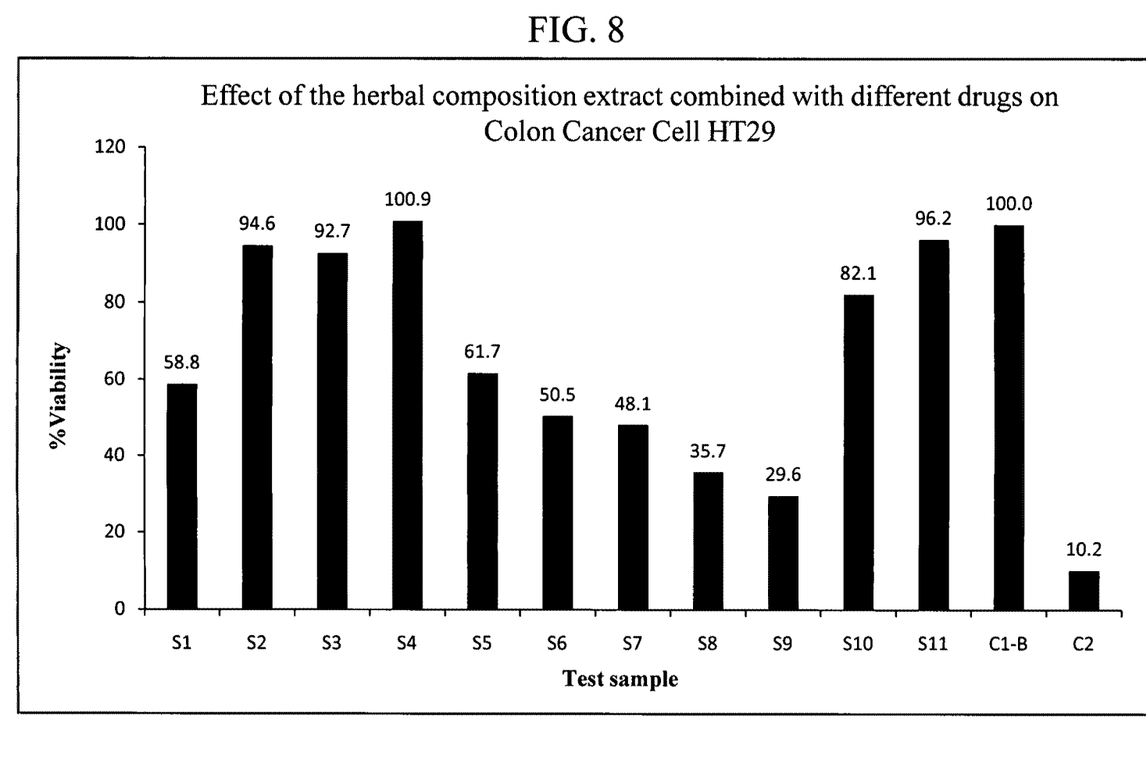
FIG. 8. shows viability of multiple drug resistant Colon Cancer Cell HT29 treated with 5 mg/ml of the herbal composition extract with/without combining different chemotherapeutic drugs.

FIG. 8 shows that the herbal composition really has good cytotoxicity on cancer cell (even on multiple drug resistant cancer cell) and obvious intensifying the effects of other anticancer drugs.

The therapeutic effects described herein may be accomplished through the administration of the herbal medicine "as is", or as tea, decoction, beverage, candy or other confection, enteral liquid nutritional products such as infant formula and adult nutritional product, medical food, nutritional supplement or neutraceutical. For pharmaceutical preparation may be administered in unit dosage forms such as capsules, packets or tablets, with or without controlled-release coating(s).

INDUSTRIAL APPLICABILITY

The instant invention is directed in part, to the discovery that specific medicinal plants or herbal medicines or their mixtures possess surprising anticancer activities. More specifically, the composition of the present invention is derived from various Chinese herbal medicines or medicinal plants which have a long history of human consumption. They are GRAS (generally recognized as safe.) There are many side effects of chemotherapy such as fatigue, nausea, constipation, diarrhea, oral ulcer, hair loss, skin itching and exfoliation, neuromuscular paralysis, hear loss, hematological problem and infertility. There are also many side effects of radiotherapy such as fatigue, hematological problem, oral pain, altered taste, dysphagia, nausea, and vomiting, anorexia, body weight loss, hoarseness, constipation or diarrhea, hear loss, skin itching and exfoliation, and infertility. The above recited side effects often disturb the cancer patients and let them be so painful. Besides, the original normal cells killed by chemotherapy or radiotherapy can produce WNT16B that may promote cancer cell growth, metastasis and therapy resistance. See Yu Sun et al., Treatment-induced damage to the tumor microenvironment promotes prostate cancer therapy resistance through WNT16B, Nat Med. September 2012; 18(9): 1359-1368. Among the eight herbs of the composition of this invention five herbs (PRUNELLAE SPICA, *ANTRODIA CAMPHORATA*, CURCUMAE RHIZOMA, *IXERIS* HERBA and *PHELLINUS LINTEUS*) have been approved by the health authority in Taiwan to be used as food ingredient. The other three herbs (SCUTELLARIAE BARBATAE HERBA, PAEONIAE SUFFRUTICOSAE CORTEX and PATRINIAE HERBA) have been commonly using by Chinese medicine physicians since ancient ages. Therefore the safety of the composition of this invention is rather obvious.

According to The Lancet Oncology report, Prof Jean-François Bosset said: "Adjuvant fluorouracil-based chemotherapy after preoperative radiotherapy (with or without chemotherapy) does not affect disease-free survival or overall survival. Our trial does not support the current practice of adjuvant chemotherapy after preoperative radiotherapy with or without chemotherapy. New treatment strategies incorporating neoadjuvant chemotherapy are required." See Prof Jean-François Bosset et al., Fluorouracil-based adjuvant chemotherapy after preoperative chemoradiotherapy in rectal cancer: long-term results of the EORTC 22921 randomized study, The Lancet Oncology, February 2014; 15(2); 184~190. And the composition of this invention revealed obvious intensifying the effects of other anticancer drugs will meet the needs to be a neoadjuvant agent for cancer chemotherapy.

According to WHO's World Cancer Report 2014, cancer will become a significantly larger global health care burden in the next 2 decades, with incidence expected to rise by 57% and deaths projected to increase by 63%. Global battle against cancer won't be won with treatment alone. Effective prevention measures urgently needed to prevent cancer crisis. See Stewart B W, Wild C P, editors (2014). WHO's World Cancer Report 2014, Because of its safety and its good cytotoxicities on cancer cells, this invention will meet the urgent needs to treat cancer and prevent cancer. So the industrial applicability of the composition of this invention is very obvious.

The medical community is constantly in search of methods and products that will effectively prevent cancer or treat cancer or reduce the severity of cancer. This composition will be readily accepted by the medical community as an additional tool in prevention and treatment of these devastating illnesses. Especially, this composition of this invention reveals obvious intensifying the effects of other anticancer drugs. In addition, more people prefer more moderate Traditional Chinese Medicine for cancer treatment.

While certain representative embodiments have been described herein, it will be apparent to those skilled in the art that various changes and modifications may be made therein without departing from the spirit or scope of this invention.

We claim:

1. A method for treating cancer, said method comprising administering to a subject in need thereof a composition consisting of therapeutically effective amounts of aqueous extracts of *Prunellae spica, Scutellariae barbatae herba, Antrodia camphorata, Curcumae rhizoma, Paeoniae suffruticosae cortex, Patriniae herba, Ixeris herba* and *Phellinus linteus*.

2. A method of claim 1, wherein the weight ratio of the aqueous extracts of *Prunellae spica:Scutellariae barbatae herba:Antrodia camphorata:Curcumae rhizoma:Paeoniae suffruticosae cortex:Patriniae herba:Ixeris herba:Phellinus linteus* is about 0.5~1.5:0.5~1.5:0.5~1.5:0.5~1.5:0.5~1.5: 0.5~1.5:0.5~1.5:0.5~1.5, respectively.

3. The method of claim 1, wherein the composition is administered in a dosage of 0.4 to 120 grams per day.

4. The method of claim 1, wherein the composition is administered orally, nasally, cutaneously, parenterally, anally, vaginally, ocularly, aurally, by spray inhalation, by implanted reservoir or by acupuncture.

5. The method of claim 1, wherein said composition is in a form selected from the group consisting of pills, tablets, jellies, lozenges, powders, candies, confections, gels, nutritional supplements, chewing gums, medical nutritionals, beverages, yogurts, milk and aqueous solutions, a nutritional product or a pharmaceutical product.

* * * * *